(12) United States Patent
Merced-O'Neill

(10) Patent No.: US 8,545,485 B2
(45) Date of Patent: Oct. 1, 2013

(54) NERVE ELEVATOR AND METHOD OF USE

(75) Inventor: Orlando Merced-O'Neill, Alachua, FL (US)

(73) Assignee: Axogen, Inc., Alachua, FL (US)

(*) Notice: Subject to any disclaimer, the term of this patent is extended or adjusted under 35 U.S.C. 154(b) by 1113 days.

(21) Appl. No.: 12/427,494

(22) Filed: Apr. 21, 2009

(65) Prior Publication Data

US 2009/0264871 A1    Oct. 22, 2009

Related U.S. Application Data

(60) Provisional application No. 61/125,086, filed on Apr. 21, 2008.

(51) Int. Cl.
*A61B 17/00* (2006.01)

(52) U.S. Cl.
USPC .............................................. 606/1; 600/210

(58) Field of Classification Search
USPC ........... 606/1, 96, 150, 159, 167, 170; 600/1, 600/210
See application file for complete search history.

(56) References Cited

U.S. PATENT DOCUMENTS

| 5,026,383 | A | * | 6/1991 | Nobles | 606/159 |
| 6,193,653 | B1 | | 2/2001 | Evans et al. | |
| 6,592,588 | B1 | * | 7/2003 | Bobic et al. | 606/79 |

FOREIGN PATENT DOCUMENTS

| DE | 35 25 917 | 2/1986 |
| DE | 197 54 779 | 6/1999 |
| WO | WO 00/42918 | 7/2000 |

* cited by examiner

*Primary Examiner* — Victor Nguyen
(74) *Attorney, Agent, or Firm* — Saliwanchik, Lloyd & Eisenschenk

(57) ABSTRACT

A nerve elevator tool is disclosed for the recovery of nerve tissue from living or cadaveric donors with minimal or no damage to internal tissues or the external integrity of the body. The elevator tool includes a dissecting head affixed to a shaft with a handle. Advancing the dissecting head through the body with the attached shaft and handle causes the elevator to "strip" tissues and structures from around the nerve and transect or rupture nerve branches with minimal avulsion, which then pass over and around the dissecting head. Once a sufficient section of nerve has been stripped, the second end of the nerve can be transected to completely free the nerve section, which can then be removed.

14 Claims, 7 Drawing Sheets

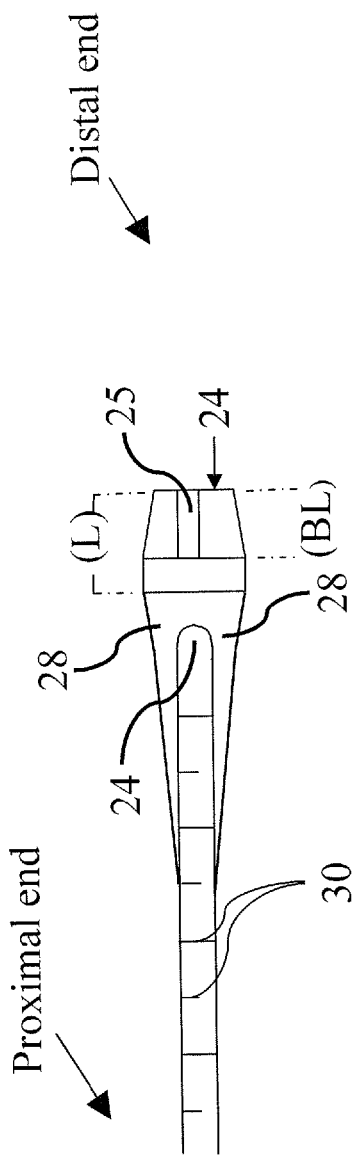
FIG. 2B
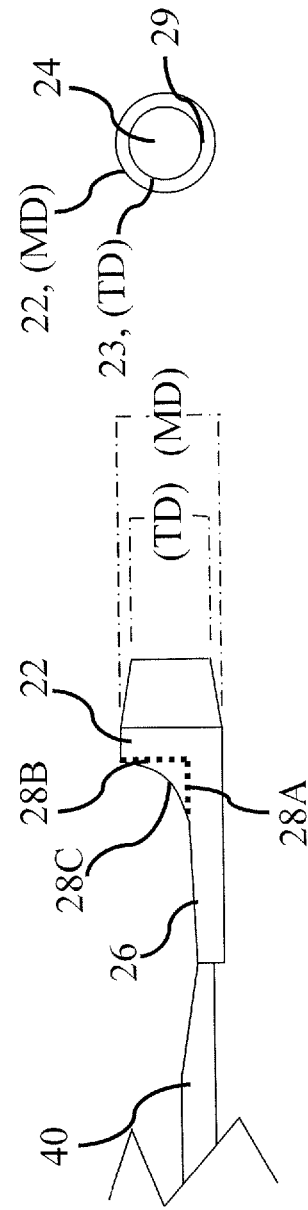
FIG. 2A
FIG. 2C

NERVE ELEVATOR AND METHOD OF USE

CROSS-REFERENCE TO A RELATED APPLICATION

This application claims the benefit of U.S. provisional application Ser. No. 61/125,086, filed Apr. 21, 2008, which is incorporated herein by reference in its entirety.

BACKGROUND OF INVENTION

The use of transplant tissues and organs in reconstructive and regenerative surgery is well-known. There are over 100 tissue banks currently in the U.S. that recover tissue from more than 25,000 donors and distribute in excess of 1.5 million allografts for transplant annually. However, the routine recovery of nerve tissue from cadaveric donors is a recent development in the tissue bank industry. Furthermore, recovery of nerve tissue, in particular lower arm nerve tissue, by minimally invasive procedures is not currently easily achieved.

Usually nerve tissue from a living donor or cadaver entails making large incisions in the body along the path of a nerve. In the case of a live donor, such large incisions are more prone to infections, tissue necrosis, swelling, scarring, poor healing, and long-lasting residual pain due to collateral tissue damage. Harvesting tissue from a cadaver is usually done soon after death and, obviously, before the body is embalmed. Thus, it can be important for aesthetic and other reasons to cause as little disruption or damage as possible to the body. The integrity of the cadaveric arterial system must especially be maintained so that the body can be properly embalmed. It can also be preferable to avoid disruption of the anatomical features as much as possible.

There are a variety of devices and tools that have been developed for obtaining donor tissues with minimal scarring and tissue disruption. For example, U.S. Pat. No. 7,320,687 discloses a "tendon stripper" and cutting device for harvesting tendons that requires a single, relatively small incision. A distal guide on the tendon stripper is placed around a donor tendon, or portion thereof, and gently pushed through the tissues with a rod, guided by the tendon. As it moves along the tendon, the distal guide pushes aside or "strips" by displacing and/or separating surrounding tissues from the donor tendon. After a sufficient length of tendon has been "stripped", an electrical cautery wire on the device severs the end of the tendon within the body allowing the tendon to be removed from the body, leaving the surrounding tissues essentially intact and in place.

U.S. Pat. No. 7,163,547 discloses a device for harvesting veins from a body, in particular the saphenous vein in the upper leg. The tip end of this device is also inserted through an incision and placed around the end of a severed and tied vein. The tip end of the device is advanced through the leg tissues, guided by the vein. The end of the device has one or more cutting edges to separate the vein from surrounding tissues and/or sever branches therefrom. Once a sufficient portion of vein has been separated, the end of tip end is palpated to locate the tip end and the end of the donor vein. The vein at this site is tied and severed. The dissected portion of vein can then be removed from the body without avulsing surrounding or previously attached tissues or branches. An elongated needle can also be used to inject a local anesthetic during use.

While each of these devices is acceptable for their intended use, their designs and the designs of similar instruments, are not conducive to harvesting delicate nerve tissue. In fact, it has been documented that the use of tendon strippers, such as the one discussed above, often results in epineural nerve damage, as well as short or unpredictable nerve lengths. (Jaroszynski, G. and Johnston, G. H. F., "Harvesting of Sural Nerve with a Tendon Stripper", 1996, *Microsurgery* 17:217-220.)

BRIEF SUMMARY

The subject invention provides devices and methods for obtaining undamaged or minimally damaged nerve tissue without avulsing surrounding vasculature, nerve branches or other tissues. In preferred embodiments, the subject devices employ a dissecting head having a lumen with two opposite, open ends especially suited for the displacement, isolation and/or separation of muscles, vasculature, connective tissues, and other structures surrounding a nerve. The leading end of the dissecting head can also be sufficiently blunted to prevent damage or premature severing of the nerve during dissection, but is capable of cutting nerves or other tissues when proper action is exerted at an appropriate angle against the tissue.

In preferred embodiments, the subject invention provides nerve elevator tools and methods for harvesting or "stripping" nerve(s) from a living donor or cadaver. The devices and methods of the subject invention facilitate the recovery of transplantable nerve tissue with minimal disruption of the adjacent vasculature, tissues, or other structures of the donor. While particularly suited for obtaining nerves from closed body donors and patients, the devices and methods of the subject invention can also be utilized with open body or open cavity procedures.

In a specific embodiment, the nerve elevator tool includes a dissecting head affixed to a shaft with a handle. The shape and configuration of the dissecting head allows it to be easily advanced through tissues with little or no avulsing of nerve branches arising from the dissected main root of the nerve, when utilized on an extremity from a proximal (closer to the body) to a distal fashion (further from the body). The tool can also be utilized in a distal to proximal fashion, relative to an extremity. Once "stripped" with the tool, the nerve can be transected at or near the dissecting head and withdrawn from the body.

In one embodiment of a method of use, a nerve to be recovered is located through an incision at or near the proximal or distal end of an extremity. The nerve can then be severed and the end inserted through the lumen in the dissecting head. The tool can then be driven along the path of the nerve by manual pressure exerted on the shaft. The nerve's orientation within the body guides the path of the dissecting head, which displaces and separates, or "strips" adjacent muscles, vasculature, connective tissue and other structures from around the nerve. Any side branches of the nerve are transected collected towards the root or ruptured by the edges of the dissecting head and lumen, causing minimal or no avulsion of the tissues.

The device and method can be used to harvest nerves from a variety of locations within a body. Advantageously, it is particularly suited for use in the lower arm because of the ability to harvest nerves with minimal disruption of the anatomical features preserving the natural appearance of the arm, which is an important concern for living donors to minimize scars and for cadaveric donors to allow for more funeral viewing options (e.g. open casket, short sleeve clothing). It also minimizes disruption to the vascular system which is vital to later proper embalming and/or preservation of viable tissue.

BRIEF DESCRIPTION OF DRAWINGS

In order that a more precise understanding of the subject invention be obtained, a more particular description of the invention briefly described above will be rendered by reference to specific embodiments thereof that are illustrated in the appended drawings. Understanding that these drawings depict only typical embodiments of the invention and are not, therefore, to be considered as limiting in scope, the invention will be described and explained with additional specificity and detail through the use of the accompanying drawings in which:

FIG. 2A is an enlarged illustration of the side view of an embodiment of the nerve elevator tool of the subject invention.

FIG. 2B is an illustration of a top view of the distal end of the embodiment shown in FIG. 2A.

FIG. 2C is an illustration of a distal end view of the embodiment shown in FIG. 1A.

DETAILED DISCLOSURE

The subject invention provides devices and methods for surgical recovery of peripheral nerves from a donor. More specifically, the subject invention pertains to a nerve elevator tool for "stripping" nerves within a cadaver or living donor. The devices and methods of the subject invention can be used with open or closed body dissections. Advantageously, the tools and methods of the subject invention can be used to minimize or eliminate damage to the donor nerve and surrounding tissues, as well as aid in preserving the internal and external integrity and vasculature of the body. The devices and methods of the subject invention can also be utilized with the same advantages for nerve treatment and/or manipulation in a living patient.

The term "donor" or "patient" as used herein, refers to a living animal or cadaver, including mammals to which the devices and methods of the present invention can be applied. Mammalian species that can benefit from the disclosed devices and methods include, but are not limited to, apes, chimpanzees, orangutans, humans, monkeys, macaques, marsupials; domesticated animals (e.g., pets) such as dogs and cats; veterinary uses for large animals such as cattle, horses, goats, sheep; and any wild animal for veterinary or dissecting purposes.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

With reference to the attached figures, which show certain embodiments of the subject invention, it can be seen that, in one embodiment, the tool 10 of subject invention comprises a dissecting head 20 fixedly attached to the distal end of a shaft 40 that has an elongated handle 60 attached to the proximal end.

Figure 1:
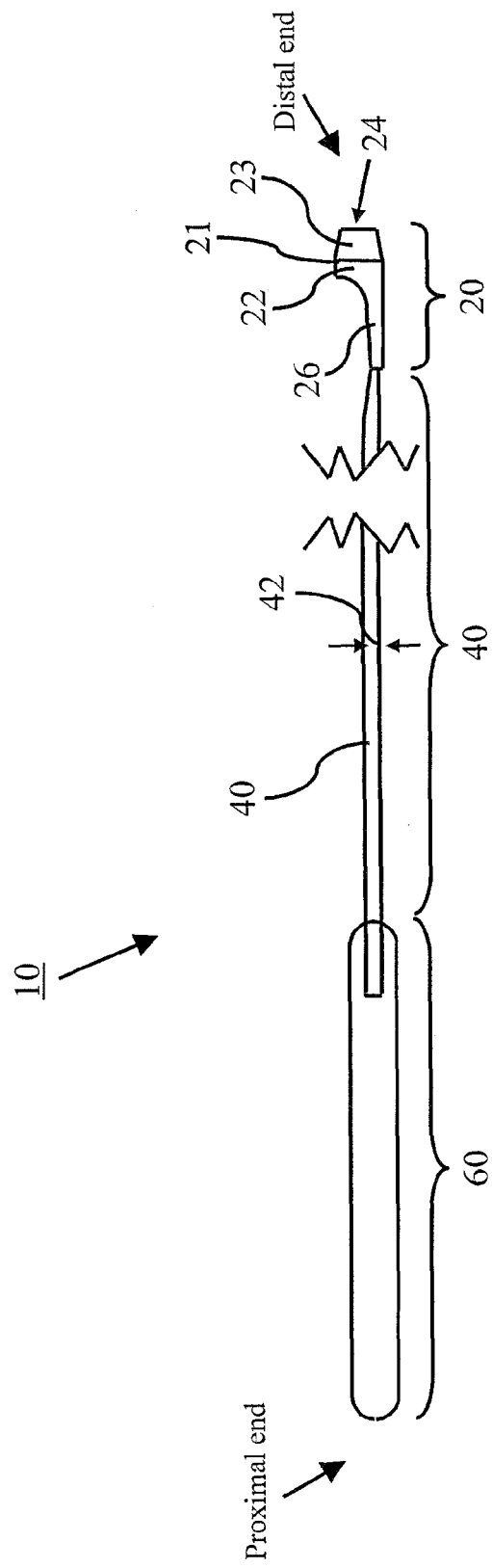
FIG. 1 is an illustration of a side view of an embodiment of the nerve elevator tool of the subject invention.
Figure 2D:
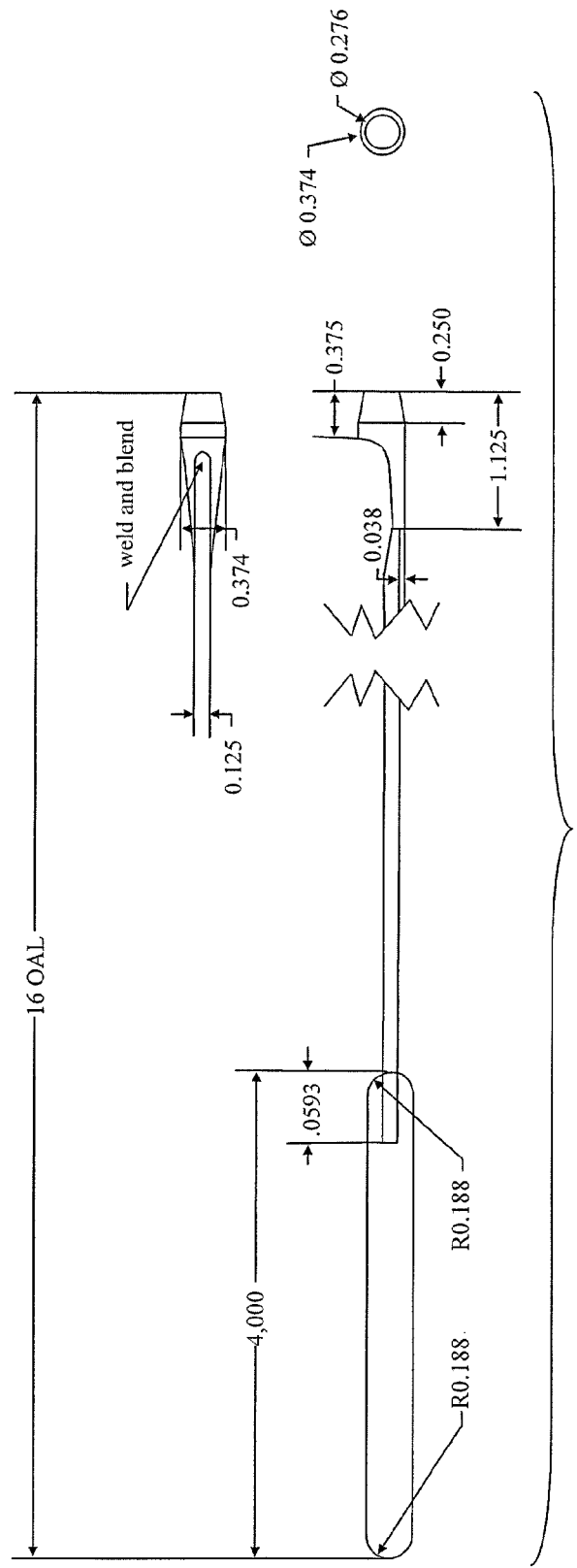
FIG. 2D is an illustration of one exemplary embodiment of the nerve elevator tool of the subject invention.
Figure 5:
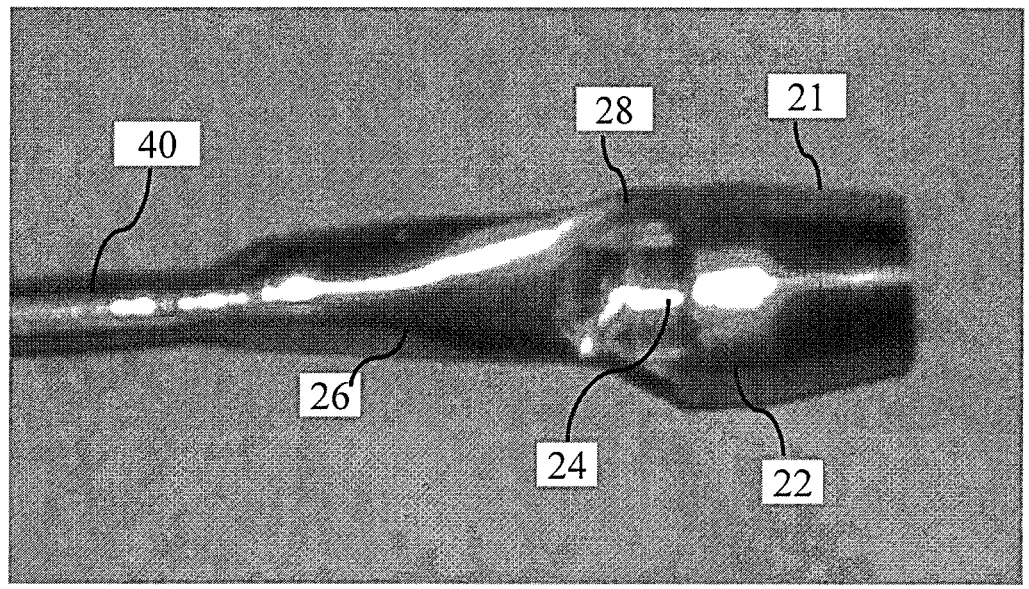
FIG. 5 is a photograph of an enlarged top plan view of the dissecting head of the embodiment shown in FIG. 3.
Figure 6:
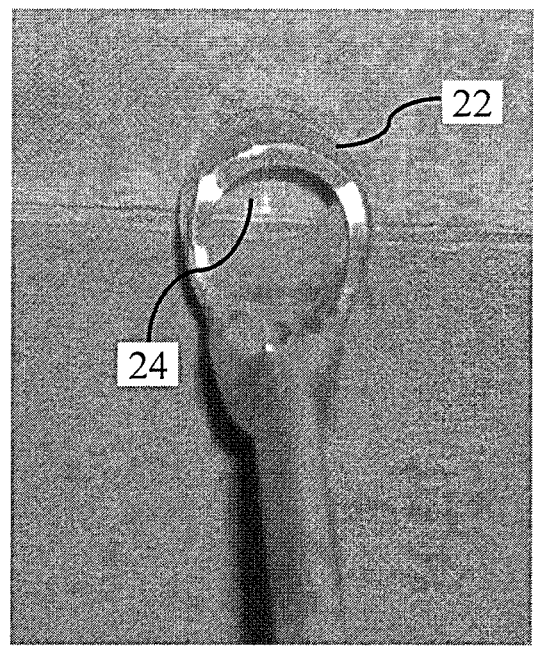
FIG. 6 is a photograph of an enlarged proximal end view of the dissecting head of the embodiment shown in FIG. 3.
Figure 7:
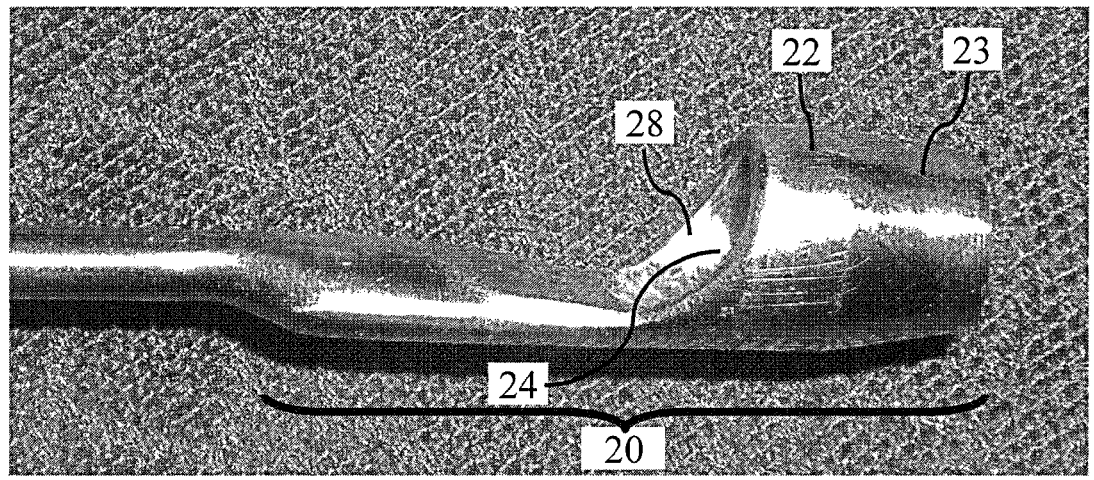
FIG. 7 is a photograph of an enlarged side view of the dissecting head of the embodiment shown in FIG. 3.
Figure 8:
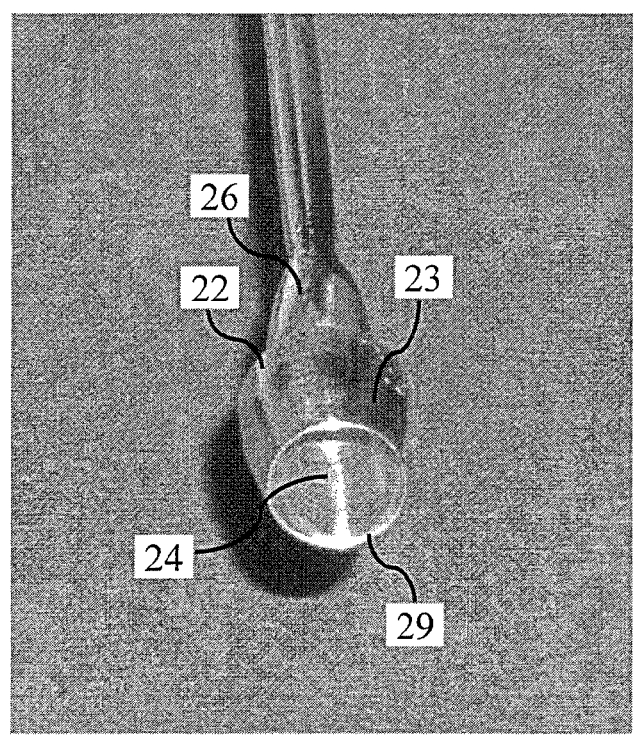
FIG. 8 is a photograph of an enlarged distal end view of the dissecting head of the embodiment shown in FIG. 3.

It can be seen in FIG. 1 that one embodiment of the dissecting head utilizes an elongated, generally conical-shaped tubular elevator 22 having a lumen 24 therethrough, providing distal and proximal open ends. In one embodiment, the diameter of the distal end of the elevator can be narrower than the diameter of the proximal end, as seen, for example in FIGS. 1 and 2A-C. In one embodiment, for example, as shown in FIGS. 2A, 2B, and 5, the outer surface 21 of the entire length, or at least some portion of the distal end, can have a bevel 23, whereby the distal end is narrower than the more proximal portion. In a further embodiment, the wall thickness of the elevator at the distal end can be less than the wall thickness at the proximal end. In a still further embodiment, the wall thickness at the distal end can have a bevel 23 that is sufficiently tapered towards the lumen to form a cutting edge 29 at the distal end, for example, as shown in FIGS. 2C and 8. In one embodiment, a bevel 23 at the distal edge can be appropriately angled so that the wall thickness at the distal edge of the elevator forms a cutting edge 29. The wall thickness of the dissecting head can be, for example, from approximately 0.01 mm to approximately 20 mm with or without tapering of the dissecting head. The conical shape can be attained by transitionally reducing the thickness of one end to a desired thickness along the body of the dissecting head. Alternatively the dissecting head can be forged in a previously made mold. Advantageously, the conical shape of the elevator 22 allows displacement or separation of tissues and structures that surround a nerve and causes them to move over and around the elevator as it is guided through a body.

The dimensions of the elevator can vary depending upon the type, diameter and location of a nerve to be recovered, as well as other factors known to those with skill in the art. In one embodiment, shown for example in FIG. 2A, the elevator can have an overall length (L) of approximately 2.5 mm to approximately 40 mm. In a further embodiment, the elevator can have a length (L) of approximately 9 mmy. The diameter (MD) of the elevator can also vary and in one embodiment is between approximately 7 mm and approximately 10 mm. In a further embodiment, the diameter (MD) of the elevator is approximately 9 mm.

As mentioned above, in one embodiment, the distal end of the elevator can be narrower than the proximal end. Thus, in one embodiment, the distal end of the elevator 22 can have a tapered diameter (TD) of approximately 5. mm to approximately 8 mm. In a more specific embodiment, the distal end can have a tapered diameter (TD) of approximately 7 mm. To achieve a narrower distal end, in one embodiment mentioned above, the outer surface 21 of the distal end can have a bevel 23 there around. In one embodiment, the bevel length (BL) can be approximately 5 mm to approximately 8 mm and tapered towards the distal end of the elevator. In a further embodiment, bevel length (BL) can be at least 6 mm and tapered towards the distal end of the elevator, wherein the angle of the bevel that would provide the above-mentioned dimensions, or a blunting edge 29 at the most distal end of the elevator, can be determined by a person skilled in the art.

Figure 4:
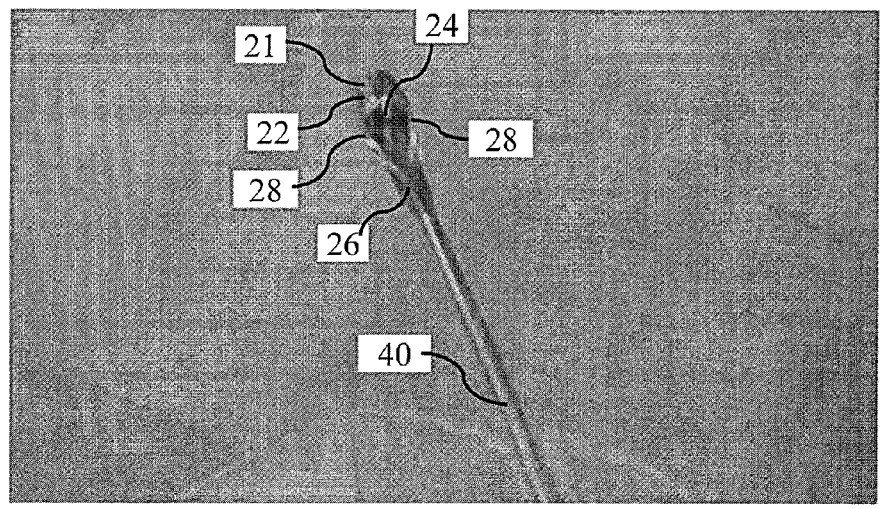
FIG. 4 is a photograph of the proximal end of the dissecting head of the embodiment shown in FIG. 3.

A lumen 24 traverses through the elevator from the distal end to the proximal end, such that there are two open ends in the elevator, as shown, for example, in FIGS. 2B and 4. The diameter of the lumen can depend upon the diameter and location of nerve tissue to be recovered, as well as other factors known to those with skill in the art. In one embodiment, the length of the lumen is centered relative to the length elevator. In alternative embodiment, the length of the lumen, or a portion thereof, is off-center relative to the length of the elevator, such that the center of the lumen and the center of the elevator are different and wall thickness along one side may be greater in one area than in another. In one embodiment, the diameter of the lumen 24 is uniform throughout the length of the elevator. That is, the lumen can be generally a tubular opening having the same diameter from the distal to the proximal end. In a further embodiment, the uniform diameter of the lumen is between approximately 5 mm and approximately 8 mm. In a still further embodiment, the diameter of the lumen is approximately 6 mm to 7 mm.

Alternatively, the lumen 24 can be of variable diameter along the length of the elevator. For example, in one embodiment, the lumen is conical, such that the diameter at the proximal end of the elevator is larger than the diameter at the distal end of the elevator. In this embodiment, the diameter of the distal and proximal ends can be determined by a person skilled in the art.

The circumferential shape of the lumen can be variable and depend upon the size, type, and location of nerve tissue to be dissected or recovered, as well as other factors that would be understood by a person skilled in the art. By way of non-limiting examples, the circumferential shape of the lumen can be ovoid, circular, square, rectangular, triangular, or any of various other polygonal shapes. In an exemplified embodiment, the circumferential shape of the lumen is generally circular. As will be discussed below, the nerve to be dissected is positioned within the lumen and can guide the direction of the dissecting head as it is advanced within the body.

In an exemplified embodiment of the elevator, shown in FIGS. 2D, and 3-8 the elevator has a length (L) of approximately 9 mm and a diameter (height) at the proximal end of approximately 9 mm. In a further exemplified embodiment, the distal end has a bevel (BL) of approximately 6 mm in length, tapering towards the distal end to a tapered diameter (TD) of approximately 7 mm. In a further exemplified embodiment, the lumen is centered in the elevator and has a diameter of approximately 7 mm. along the entire length.

In a further embodiment, the elevator 22 can be modified with a lengthwise slit 25 that extends from the distal end to the proximal end and through the elevator of the lumen 24. The slit can allow a nerve to be placed within or removed from the lumen without being severed. The dimensions of the slit can vary depending upon the dimensions of the elevator and the anticipated diameter of the nerve to be dissected. In a specific embodiment, the slit 25 has a width sufficient to allow passage of the nerve therethrough without damage. The slit can be located at any point around the circumference of the elevator. In a specific embodiment, the slit is located on the elevator substantially opposite to the location of attachment of the shaft 40 to the elevator, discussed below. In a further embodiment, the slit is generally parallel to the shaft 40. In an alternative embodiment, the slit is located on one side of the elevator. In a further alternative embodiment, the slit is cross-cut within the elevator, such that it is not parallel to the shaft 40.

In a further embodiment, extending from and integral with the proximal end of the elevator 22 is an extension 26, which can be fixedly coupled to a shaft 40. In one embodiment, the extension can be a flange-like protrusion integrated with the proximal edge of the elevator. In a further embodiment, the extension 26 is sufficiently sturdy to support a shaft fixedly attached at or near the proximal end of the extension. In a still further embodiment, the extension has sufficient rigidity to reduce or eliminate bending between the extension and an attached shaft 40.

To ensure sufficient rigidity and lend additional support to the extension, the distal end can be flared or broadened, so that there is a larger fixed connection with the proximal edge of the elevator. In one embodiment, the extension is formed with or made to include gussets 28 on one or both sides of the extension 26, as shown, for example in FIGS. 2A, 2B, and 4. The one or more gussets 28 can be formed or attached so that a first side 28A is integral with the extension and a second side 28B is integral with the proximal edge of the elevator 22.

In a further embodiment, a third side 28C can be formed with a smooth, slightly concave curved edge, as seen in the Figures. The curvature of the proximal edge of a gusset 28C can be beneficial in protecting and supporting the stripped nerve tissue as it passes through the lumen 24, ease the passage of the elevator through tissues and, further, aid in the retraction of the dissecting head from the body through the first opening with minimal or no damage to tissues.

The length of the extension 26 can be variable with regard to the type of materials utilized, thickness of the materials, dimensions of the gussets, and other factors known to those with skill in the art. In one embodiment, the extension length can be between approximately 13 mm and approximately 25 mm. In an exemplified embodiment, shown for example in FIGS. 2D, 4, and 5, the extension length is approximately 20 mm in length.

The dissecting head can comprise any of a variety of materials suitable for use in recovering tissues from a donor. In one embodiment, the dissecting head is manufactured from a biocompatible material suitable for use with a living donor, as well as cadaveric recoveries. In one embodiment, the elevator is manufactured from stainless steel, such as, for example, a 316 or 316L (medical) grade stainless steel. In a further embodiment, the stainless steel can undergo passivation with citric acid or nitric acid treatment, as known to those with skill in the art, to reduce chemical reaction within the body. A person with skill in the art, having benefit of the subject disclosure, would be able to determine any of a variety of materials that would be suitable for use with the embodiments of the subject invention and such variations are considered to be within the scope of the subject invention.

In order to advance the dissecting head 20 through a body, a shaft 40 can be fixedly attached at or near the proximal end of the extension 26. The shaft 40 can be of any desirable length depending upon the type and location of nerve tissue to be recovered, as well as other factors known to those with skill in the art. While the device of subject invention can be used in a variety of locations within the body, including the head and torso, it can be particularly useful for the recovery of nerve tissue from the extremities, e.g., arm or leg, of a donor. Thus, in one embodiment, the length of the shaft 40 is between approximately 15 cm and approximately 36 cm. In a further embodiment, the length of the shaft 40 is between approximately 25 cm and approximately 33 cm. And, in an exemplified embodiment, shown for example in FIGS. 1, 2D, and 3, the length of the shaft is approximately 30 cm. However, it should be recognized that the length of the shaft can vary depending upon the expected location of use within the body.

During the extraction of a nerve, it can be important for the shaft 40 to maintain rigidity, so that it is not easily deflected by tissues or structures within the body, as it follows the path of the selected nerve. In an exemplified embodiment, the shaft provides sufficient support for the dissecting head 10 to move past and deflect or separate tissues and structures around a nerve, so that they can move over and around the dissecting head. In a further embodiment, the shaft has sufficient strength and rigidity to push the distal end of the elevator 22 with sufficient force to rupture or transect nerve branches, or collect some portion of nerve branches extending from the main nerve trunk.

On the other hand, it can be helpful for the shaft to have a certain amount of flexibility to permit movement around bodily structures, to more easily follow the path of a nerve, and/or to assist with extraction of the device from the body. In one embodiment, the shaft comprises one or more materials that impart the necessary rigidity for manipulating the dissecting head and sufficient flexibility. In an alternative embodiment, the shaft comprises one or more generally flexible materials that are fully or partially surrounded and supported by a sufficiently rigid material. The flexible shaft is to allow the dissecting head to go around rigid/hard structures such as bone. An example, in the case of the radial nerve—starting distally at the humoral epicondyle the nerve travels around the bony prominence and advances proximally behind the humoral shaft going medially towards the thoracic outlet where it joins all other brachial plexus derived nerves. A flexible shaft allows for the dissecting head to be advanced around the humoral shaft resulting in the release of the nerve from the adjacent tissue without major disruption to this tissue, or necessitating a number of incisions to track the nerve path. In a particular embodiment, the generally flexible shaft is surrounded by a sleeve of rigid material. The sleeve stiffens the shaft to allow advancement and when retracted allows dissecting head to travel in a non-linear fashion.

In a still further embodiment, the overall shaft diameter 42 is relatively small to prevent damage to surrounding tissues and structures. This may be particularly important if the tool is to be passed through the body for extraction at a second incision. Thus, in one embodiment, the shaft diameter 42 can be between approximately 1 mm to approximately 4 mm. In an exemplified embodiment, shown for example in FIGS. 2D and 3, a shaft of the subject invention has a diameter of approximately 3 mm.

In a further embodiment, the shaft comprises the same or a different material than the dissecting head. In a further embodiment, the shaft comprises a stainless steel, such as the 316 or 316L (medical) grade stainless steel. In a further embodiment, the stainless steel undergoes passivation by, for example, a citric acid or nitric acid treatment, as known to those with skill in the art, to reduce chemical reaction with tissues in a body. A person with skill in the art and benefit of the subject disclosure would be able to determine from any of a variety of materials one or more that would be suitable for use in a body and capable of providing sufficient rigidity to a shaft with minimal diameter, and such variations are contemplated to be within the scope of the subject invention.

Figure 3:
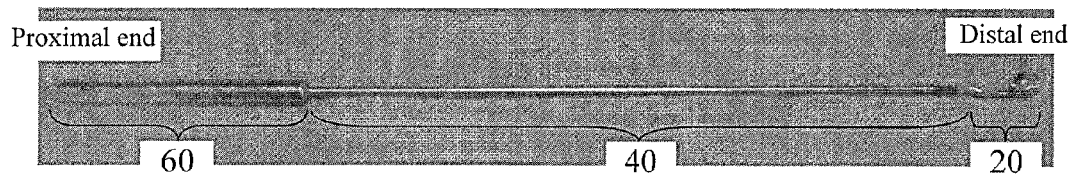
FIG. 3 is a photograph of an exemplary embodiment of the nerve elevator tool of the subject invention.

The distal end of the shaft 40 can be attached to the extension 26 by any variety of techniques and devices known to a person with skill in the art. For example, the shaft can be riveted or bolted to the extension. In another embodiment, the shaft is affixed to the extension by means of a threaded connection whereby the shaft and extension are screwed together. Still further, any of a variety of suitable adhesives or epoxies can be used to fixedly connect the shaft and the extension. In a yet further embodiment, the distal end of the shaft 40 is fixedly and immovably attached at or near the proximal end of the extension by means of welding, whereby the material of the shaft can be all or partially blended and/or embedded with the material of the extension. FIGS. 2B, 3, and 4 illustrate example embodiments where the shaft is welded to the extension. Preferably, any connection employed between the extension 26 and the shaft 40 will be sufficiently secure to prevent detachment during a procedure and provide a surface that can minimize or prevent damage to a nerve as it passes through the lumen 24 or to surrounding tissues or structures.

In addition to the integrity of nerve tissue, the length of the nerve segment recovered can be important to the success of transplantation. There are a variety of devices that are used, in vivo and/or ex vivo, to measure various types of tissues, including nerve tissues. Some devices utilize a visual reading, such as, for example, calipers, rulers, depth probes, segmometers, anthropometers, measuring tapes, measuring boards, and various other devices having graduations or indicators to visually determine the length and/or diameter of nerve tissue. Other devices, known to those with skill in the art, utilize chemical and/or electrical signals transmitted through or by nerve tissue to determine the length and/or diameter of nerve tissue. Such devices can be used with the tool 10 of the subject invention to ensure that sufficient nerve tissue can be or is recovered during a procedure.

In a further embodiment, the shaft 40 of the subject invention is marked with one or more indicators that can provide a visual indication of the length of the nerve segment that has been stripped from a donor, or the distance the nerve extraction tool has been advanced in a body. In one embodiment, labeled graduations are utilized to indicate distance or length. In a further embodiment, the graduations on the shaft are calibrated so that a measurement includes the length of the dissecting head. And in a still further embodiment, the graduation divisions are sufficient to provide the required accuracy for recovering nerves. In a yet further embodiment, the shaft is marked or labeled with one or more indicators that provide information about the position or direction of the dissecting head relative to the distal end of the shaft. This can assist in determining, during a procedure, whether the dissecting head is positioned upwards or downwards relative to the shaft.

To facilitate handling and manipulation of the device of the subject invention, any of a variety of styles and types of handles can be formed or attached to the proximal end of the shaft. For example, in one embodiment, the handle comprises the same or similar material as the shaft, as described above. In a still further embodiment, the handle is affixed to the shaft by any of a variety of techniques including, but not limited to, a threaded screw-on connection, nut and bolt connection, an adhesive or epoxy, welding, press-fitting and by means of other techniques and devices capable of securing the handle and the proximal end of the shaft. Preferably, the connection is stable with minimal or no movement between the handle and the shaft. In one embodiment, the handle can be manufactured of a stainless steel, such as the 316 or 316L (medical) grade stainless steel. In a further embodiment, the stainless steel undergoes passivation by, for example, a citric acid or nitric acid treatment, as known to those with skill in the art, to prevent chemical reaction within a body.

The length of the handle can also vary depending upon a variety of factors that would be appreciated by a person with skill in the art. In one embodiment, the handle is between approximately 7 cm and approximately 15 cm, such that the full length of the tool 10 is between approximately 38 cm and approximately 45 cm. Further to the exemplary embodiment described above and shown in FIGS. 2D and 3, the handle can be approximately 10 cm in length, such that the full length of the tool 10 can be approximately 40 cm.

Still further, the handle can comprise one or more grooves, indentations, knobs, projections, ergonomic structures or configuration, or other structures known in the art that can assist with holding and/or manipulation of the device. Such structures can be of particular importance if the tool will be retracted from the body. That is, it will be removed through the original opening or incision. However, an alternative procedure can be performed, wherein the tool 10 can be removed by advancing it through a second incision or opening. Thus, in an alternative embodiment, the handle can be generally smooth and free of any structures that can abrade, cut, pierce, rupture, or otherwise damage tissues as it is advanced through the body. In a still further embodiment, the distal end and proximal end of the handle are rounded, as shown, for example, in FIGS. 1 and 3 to ease passage through the body. In a still further embodiment, the handle can be removably attached, allowing it to be disconnected from the shaft prior to extraction or for other purposes as may be necessary during a procedure.

The shape of the handle can vary depending upon a variety of factors known to those with skill in the art. In one embodiment, the handle has a circular circumferential shape with a diameter between approximately 5 mm and approximately 20 mm. In an exemplified embodiment, shown for example in FIGS. 2D and 3, the handle circumference is approximately 10 mm.

A particular concern when recovering nerves from a cadaver can be the preservation of the vascular structures surrounding the recovered nerve to ensure proper embalming later of the body. It can also be desirable to preserve the visual integrity of the body, especially during procedures on the upper body. Also, when recovering, treating, repairing or tunneling nerves in a living donor, it is desirable to minimize scarring and disruption of tissues surrounding the nerve to be recovered or released.

The tool of the subject invention is designed to efficiently recover nerves from a living donor or cadaver, with minimal or no damage to the nerve and/or the surrounding tissues and structures. While particularly useful for harvesting nerve tissue from closed body donors or patients, the device of the subject invention can also be utilized with open or partially open body donors or patients.

Figure 9:
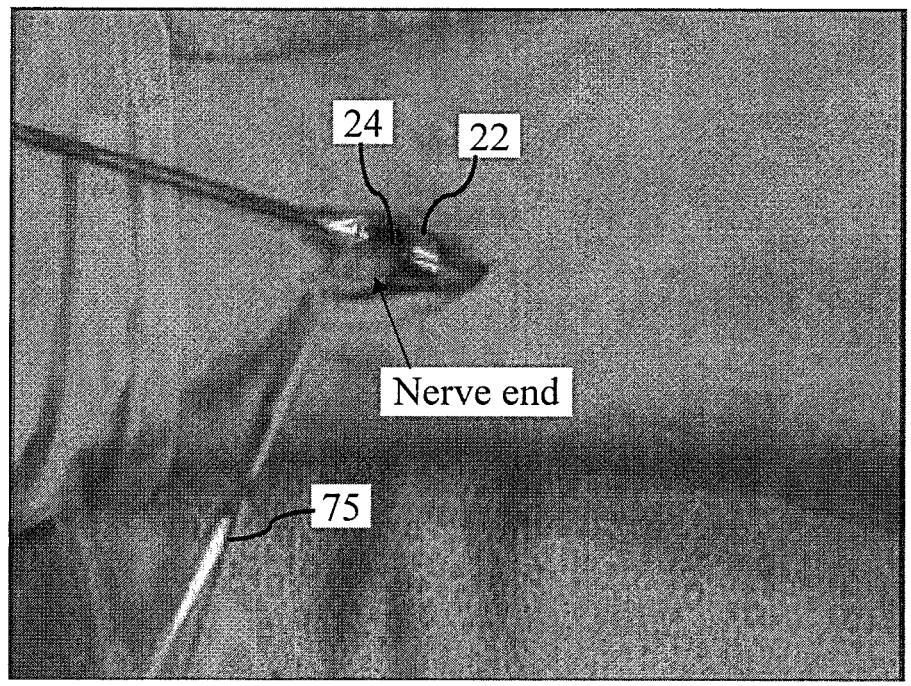
FIG. 9 is a photograph showing a transected nerve end being passed through the lumen of the dissecting head of the nerve elevator embodiment shown in FIG. 3.

Use of the tool of the subject invention with a closed body donor require a first opening in a body, such as, for example, in the distal end of the forearm. Such first opening can be pre-existing or be made by, for example, a relatively minimal incision with a scalpel, scissors, ultrasonic or laser equipment, or other suitable instrument. Once the appropriate nerve is located through the first opening, or incision, or within an open incision or cavity, it can be secured with a suture or surgical device 75, such as, for example, forceps, a hemostat, tweezers, clips, or other appropriate device, and transected to create a secured first nerve end. The transected first end of the nerve can then be passed through the distal end of the lumen 24 of the elevator. FIG. 9 shows an example of a dissected and transected nerve end being passed through the lumen 24.

Once through the lumen, the transected nerve end can again be securely held and the dissecting head 20 can be passed through the first opening. Then, by applying pressure to the handle, the dissecting head can be passed through the body being guided by and along the path of the nerve. The nerve acts similar to a guide rope passing through the lumen that leads the dissecting head along the correct path to prevent or minimize deviation into surrounding tissues. As the dissecting head is guided by and follows the nerve, tissues and structures around the nerve encountering the, distal edge of the elevator are stripped, displaced or otherwise separated from the nerve so that they pass over and around the outside of the elevator. Any side branches extending from the nerve are cut, transected, ruptured, or otherwise disconnected from the main nerve by the distal edge of the lumen 24, prior to entering the lumen, or by the distal edge of the elevator 22. During dissection, it is also possible that some nerve branches, or portions thereof, can be pulled, collected, realigned, ruptured or otherwise removed from the surrounding tissues and gathered along the main nerve trunk before being cut by the dissecting head 20.

Usually, the progress of the dissecting head within a body can be detected visually as it passes under skin and tissues. Alternatively, the location of the elevator can be palpated if not visually discernable. It is also possible to employ the use of ultrasound, X-ray, fluorescent dyes, magnetic devices, or other techniques and devices known in the art to determine the location of the dissecting head. Once the dissecting head is located, it is possible to determine the length of the nerve tissue stripped by the elevator.

Figure 10:
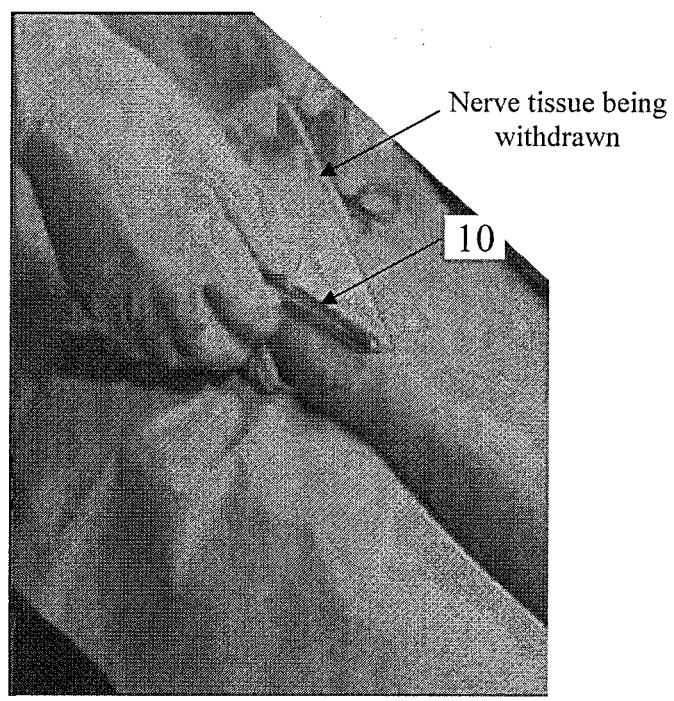
FIG. 10 is a photograph showing the withdrawal of a dissected nerve from a donor.

Once a sufficient length of nerve tissue has been stripped, the second end of the nerve must be transected to remove the length of nerve from the body. One method of accomplishing this is to locate the dissecting head and the end of the nerve and make a second incision through the body, if necessary, at or near the distal end of the dissecting head, with a scalpel, scissors, or other suitable instrument, to transect the end of the dissected nerve. After the nerve is fully dissected within the donor and the second end is transected, it can be withdrawn from the body through the first incision, as shown, for example, in FIG. 10.

An alternative method utilizes the dissecting head to transect the second end of the nerve and negates the need for a second opening. With this method, once a sufficient length of nerve has been dissected, the elevator can be turned so that the lumen is more perpendicular to the nerve. During the dissecting or stripping process, the lumen 24 is substantially collinear with the nerve, allowing the nerve to slide through the lumen with minimal or no damage. Conversely, when the dissecting head and the lumen therein are turned or rotated towards the nerve, the distal end presses against the nerve. By applying sufficient pressure as the dissecting head is pressed against the nerve, the nerve end can be severed by the cutting edge 29 of the dissecting head. This technique can be utilized in any location within the body, eliminating the need for a second incision or opening to sever the second end of the nerve. However, it has been found to be most effective when performed at a jointed area of the body. A jointed area allows for the nerve to be angulated so that the dissecting head meets the nerve at an angle allowing transection.

When using this cutting method, the angle to which the dissecting head can be rotated or turned can depend upon several factors, such as, for example, how deep the elevator is located within the body, the direction and/or position of the dissecting head within the body, and other factors known to those with skill in the art. Forcing the dissecting head to an extreme angle can cause trauma to surrounding tissues, including the area around the incision or other opening. This is an undesirable consequence, particularly with living donors. Advantageously, the elevator of the subject invention does not require an extreme angle to facilitate nerve transection. In one embodiment, the method requires the dissection head and lumen to be turned to between approximately 8° and 30° relative to the nerve to produce an adequate cutting edge. In a more particular embodiment, the method requires the dissection head and lumen to be turned to approximately 10° relative to the nerve to produce an adequate cutting edge. By applying sufficient, but not excessive pressure, at the appropriate angle, the cutting edge 29 of the dissection head can sever the nerve with minimal damage to the surrounding tissues.

In another embodiment, a cutting blade is affixed to the dissecting head and can be remotely triggered to transect the nerve. The trigger can be located at the handle. Once the desired length has been attained the operator can then actuate the trigger causing the transaction of the nerve.

Once the nerve has been harvested, the elevator can then be retracted along the same path, allowing the curvature of the proximal end and gussets 28 to displace the tissues again as it passes. Alternatively, the entire tool can continue to be advanced through the body until it is passed entirely through the second opening. This can minimize contact with internal tissues and structures and reduce the chances of damage that can be caused by a second passage of the dissecting head through and past tissues. With this method, the handle may or may not need to be removed, as described above to assist with passage through the body.

To dissect or release lengths of nerve tissue that may be longer than the length of the elevator device of the subject invention, a method using multiple access openings in conjunction with a "daisy chain" process can be used. With this method, the dissecting head can be passed along a length of nerve to an opening at the second point along the nerve length. The second point of the nerve can then be removed from the lumen 24 through the slit 25, described above, and temporarily secured. The nerve extraction tool 10 can then be removed from the body through either opening and, if desired, after removing the handle. The second point of the nerve can then be returned to the lumen through the lumen or slit and the dissecting head passed through the opening and passed along a further length of the nerve. Again, at a third opening along the nerve path the nerve can be removed from the lumen through the slit. The nerve extraction tool can then, again, be removed from the body and reinserted at the third opening after the nerve is replaced within the lumen. This process can be repeated any number of times until a sufficient length of nerve has been dissected or released from surrounding tissues.

One embodiment of the subject invention provides a surgical kit that includes one or more of the components and/or devices necessary to harvest nerve tissue. In a further embodiment, a surgical kit comprises a nerve elevator tool of the subject invention, a means for grasping and securing the end of a nerve, a means for transecting tissues, including nerve tissue; and a means for obtaining a measurement of the length of the nerve tissue. The tool of the subject invention can recover intact, undamaged nerve tissue of sufficient lengths for transplant. The tool and procedures for use minimize damage to internal and external body tissues and is, thus, suitable for use on living donors as well as cadavers.

All patents, patent applications, provisional applications, and publications referred to or cited herein are incorporated by reference in their entirety, including all figures and tables, to the extent they are not inconsistent with the explicit teachings of this specification.

It should be understood that any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such similar devices as are required. However, it is to be understood that the invention can be carried out by specifically different devices and methods, and that various modifications, both as to equipment details and methods of use can be effected without departing from the scope of the invention itself. Further, it should be understood that, although the present invention has been described with reference to specific or details of certain or exemplary embodiments thereof, it is not intended that such details should be regarded as limitations upon the scope of the invention except as and to the extent that they are included in the accompanying claims.

I claim:

1. A nerve extraction tool comprising:
a dissecting head having
an elevator comprising a slit within the elevator; said elevator with a distal end and a proximal end, where the diameter of the distal end is less than the diameter of the proximal end; a lumen extending through the elevator and open to the distal end and the proximal end of the elevator; and a shaft fixedly attached at or near the proximal end of the elevator, extending from the elevator in a direction generally parallel to the lumen; and further comprising two gussets fixedly attached between the extension and the elevator.

2. The nerve extraction tool, according to claim 1, further comprising a handle attached to the proximal end of the shaft.

3. The nerve extraction tool, according to claim 2, wherein the handle is removably attached to the shaft.

4. The nerve extraction tool, according to claim 1, further comprising an extension between the elevator and the shaft.

5. The nerve extraction tool, according to claim 1, further comprising at least one gusset fixedly attached between the extension and the elevator.

6. The nerve extraction tool, according to claim 1, wherein the circumferential shape of the lumen is circular, ovoid, triangular, square, or rectangular.

7. The nerve extraction tool, according to claim 1, wherein the lumen has a diameter of between approximately 5 mm and approximately 8 mm.

8. The nerve extraction tool, according to claim 1, wherein the lumen has a diameter of approximately 7 mm.

9. The nerve extraction tool, according to claim 1, wherein a portion of the distal end of the elevator is tapered to form a beveled end.

10. The nerve extraction tool, according to claim 9, wherein the elevator has a tapered diameter at the distal end of between approximately 6 mm and approximately 8 mm and a diameter at the proximal end of between approximately 8 mm and approximately 10 mm.

11. The nerve extraction tool, according to claim 10, wherein the beveled edge at the distal end of the elevator forms a cutting edge with the lumen.

12. The nerve extraction tool, according to claim 1, wherein the length of the shaft is between approximately 15 cm and approximately 35 cm.

13. The nerve extraction tool, according to claim 1, wherein the length of the shaft is approximately 30 cm.

14. The nerve extraction tool, according to claim 1, further comprising one or more indicators on the shaft.

\* \* \* \* \*